(12) United States Patent
Wenman

(10) Patent No.: US 6,577,140 B1
(45) Date of Patent: Jun. 10, 2003

(54) METHOD AND DEVICE FOR MEASURING THE ACIDITY OR BASICITY OF INSULATING FLUIDS, PARTICULARLY MINERAL AND SYNTHETIC OILS

(76) Inventor: Richard A. Wenman, 4500 Hiatus Rd. - Suite 206, Sunrise, FL (US) 33351

( * ) Notice: Subject to any disclaimer, the term of this patent is extended or adjusted under 35 U.S.C. 154(b) by 0 days.

(21) Appl. No.: 09/890,114

(22) PCT Filed: Jan. 26, 2000

(86) PCT No.: PCT/US00/01747

§ 371 (c)(1),
(2), (4) Date: Jul. 26, 2001

(87) PCT Pub. No.: WO00/45145

PCT Pub. Date: Aug. 3, 2000

Related U.S. Application Data

(60) Provisional application No. 60/117,388, filed on Jan. 27, 1999.

(51) Int. Cl.[7] .................. G01R 27/04; G01R 27/26; G01N 27/74
(52) U.S. Cl. .................. 324/637; 324/204; 324/690
(58) Field of Search .................. 324/637, 204, 324/690, 698, 692, 232

(56) References Cited

U.S. PATENT DOCUMENTS

| | | | | |
|---|---|---|---|---|
| 3,633,099 A | * | 1/1972 | Richman | 324/71.1 |
| 3,790,279 A | * | 2/1974 | Skala | 250/565 |
| 3,903,460 A | * | 9/1975 | Tsacoyeanes et al. | 361/327 |
| 4,646,070 A | * | 2/1987 | Yasuhara et al. | 324/690 |
| 4,741,204 A | * | 5/1988 | Luck et al. | 73/116 |
| 4,822,566 A | | 4/1989 | Newman | |
| 5,090,246 A | * | 2/1992 | Colla et al. | 73/718 |
| 5,111,698 A | * | 5/1992 | Banholzer et al. | 73/718 |
| 5,262,732 A | * | 11/1993 | Dickert et al. | 324/204 |
| 5,321,331 A | * | 6/1994 | Baer et al. | 73/718 |
| 5,604,441 A | | 2/1997 | Freese et al. | |
| 5,675,259 A | | 10/1997 | Arndt et al. | |
| 5,824,889 A | * | 10/1998 | Park et al. | 324/71.1 |
| 5,922,946 A | * | 7/1999 | Hirota et al. | 73/61.75 |
| 6,028,433 A | | 2/2000 | Cheiky-Zelina et al. | |
| 6,051,970 A | * | 4/2000 | Hutchings | 324/204 |
| 6,169,394 B1 | * | 1/2001 | Frazier et al. | 324/692 |
| 6,204,656 B1 | * | 3/2001 | Cheiky-Zelina et al. | 324/71.4 |
| 6,255,954 B1 | * | 7/2001 | Brown et al. | 324/698 |
| 6,268,737 B1 | * | 7/2001 | Marszalek | 324/663 |
| 6,278,281 B1 | * | 8/2001 | Bauer et al. | 324/668 |

* cited by examiner

*Primary Examiner*—Kamand Cuneo
*Assistant Examiner*—Jermele Hollington

(57) ABSTRACT

Method and device for monitoring an insulating or conducting test fluid for acidity, basicity, contaminants and/or specific chemicals by monitoring the rate of modification, for example corrosion, dissolution or erosion of at least one plate of a capacitive sensor immersed in the fluid. The sensor's dielectric element is inorganic or piezoelectrically active ceramic. Capacitor plates can be different materials, foil or coated/deposited metals modified by the test fluid. Capacitance is measured over time, its change due to modification of sensor plate area is recorded and used to determine quantity of acid, alkali, contaminants and/or chemicals in the test fluid. Piezoceramic dielectric allows the detector to be vibrated. The sensor can be attached to an ultrasonic transducer. Presence of specific chemicals requires a chemically non-reactive and a chemically reactive electrode re the chemical of interest. If the test fluid is conductive, the changed capacitance is measured in an insulating fluid.

22 Claims, 10 Drawing Sheets

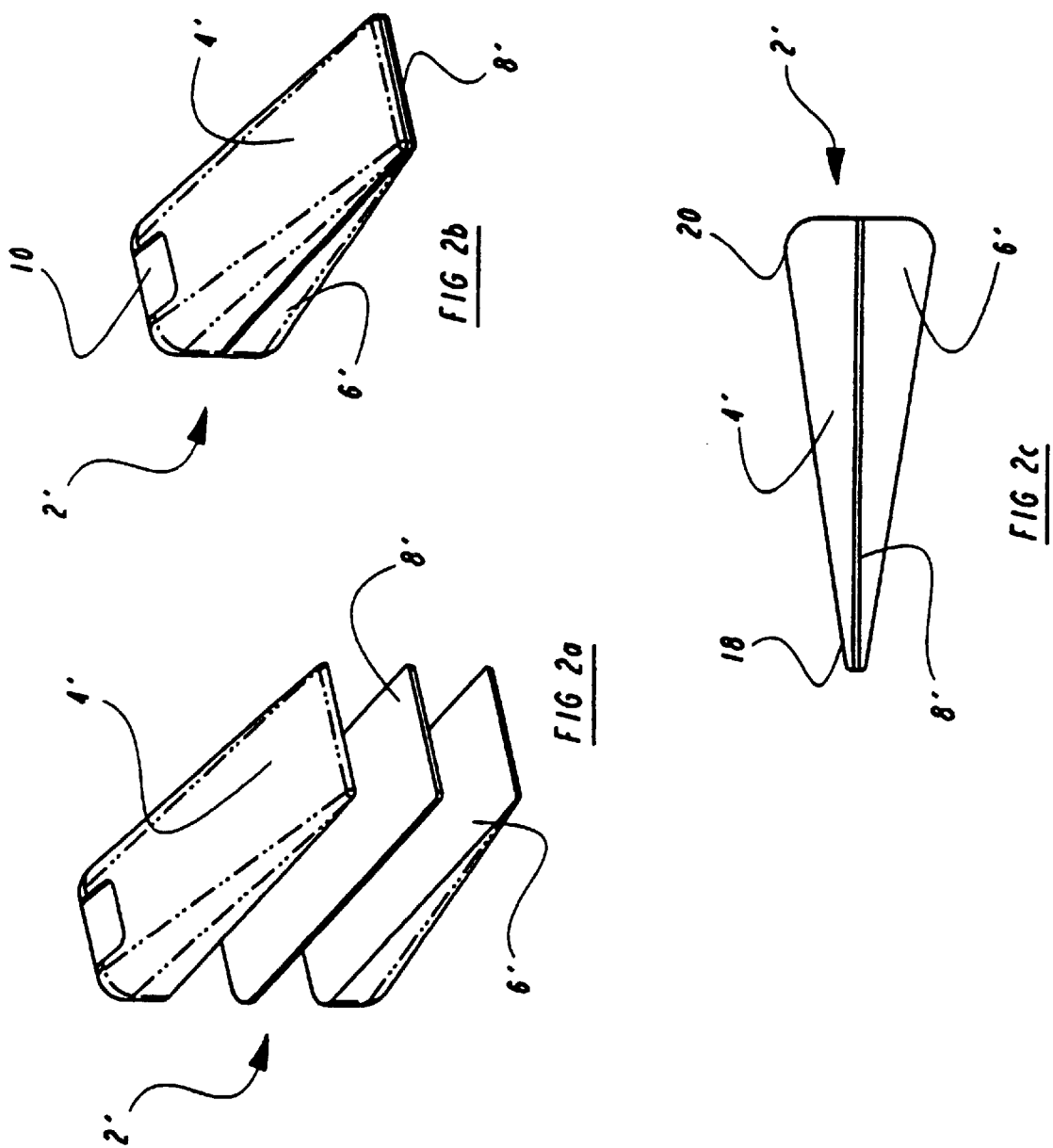

METHOD AND DEVICE FOR MEASURING THE ACIDITY OR BASICITY OF INSULATING FLUIDS, PARTICULARLY MINERAL AND SYNTHETIC OILS

CROSS-REFERENCES TO RELATED APPLICATIONS

This application claims the benefit of U.S. Provisional Application No. 60/117,388, filed Jan. 27, 1999.

BACKGROUND OF THE INVENTION

1. Field of the Invention

This invention concerns measuring characteristics, such as acidity and basicity, of insulating fluids, such as mineral oils and synthetic oils. Such measuring can monitor pipe corrosion and the degradation of internal combustion engine lubricating oil.

2. Description of the Prior Art

The acid or basic (pH) nature of fluids is important in many fields, particularly in the measurement or prevention of corrosion. For example, the transport of fluids through pipes of all sizes has generated much interest in monitoring the rate of corrosion in order to predict their life. Over the years many patents and standards have been created for the purpose of measuring corrosion rates. Much of this prior art is suitable for both electrically conducting and non-conducting fluids. Corrosion rates may be predicted from pH and other ion concentration measurements and this approach has been investigated. Specific applications, such as monitoring the degradation of internal combustion engine lubricating oil, have lead to very specific solutions.

The prior art for this invention is detailed in three sections. The first section covers the monitoring of metal corrosion in fluids. The second section concerns the monitoring of acidity/basicity (pH) of oils and other non-conductive fluids; and the third covers the measurement of oil degradation (or contamination) using capacitance measuring devices.

Corrosion

The definition of "corrosive" is specific to both the fluid and the type of material used in each application and therefore is considered being simply the science of reaction of a solid with its environment. Corrosion in engineering usually is considered the reaction of a constructional material, such as metal, with its environment with a consequent deterioration in the properties of the material. The term "corrosive" is used commonly to describe liquids or gases which are either acidic or alkaline in nature. Reference tables for metals, alloys and other engineering materials quote chemical compatibility data for mineral acids such as hydrochloric, sulfuric and nitric acid and in alkali metal bases such as potassium or sodium hydroxide.

Corrosion may be classified into the following types: Uniform, Localized, Selective Dissolution, Pitting and Interaction with a Mechanical Factor. Examples of Uniform corrosion include oxidation/tarnishing, active dissolution, anodic oxidation/passivity and chemical/electrochemical polishing. Dissolution is defined herein as the solubilization of a material. Erosion is the removal of material by some unspecified means and corrosion is a general term that encompasses dissolution, erosion and chemical reaction, such as oxidation and reduction. Localized corrosion often is due to heterogeneity in the material; and pitting occurs in passive metals in the presence of specific ions.

Many industries, such as petrochemical, chemical, pharmaceutical, and others have found it necessary to monitor the corrosion rates of fluid containers, piping, and other components used within corrosive environments. Component lifetime can be predicted and down time can be avoided by careful monitoring of the corrosion of critical components.

One of the first methods used for measuring corrosion was to detect the resistance changes within a piece of metal immersed in the corrosive liquid. The resistance of this sacrificial piece of metal changed with time and one embodiment of the method is described in U.S. Pat. No. 3,857,094 Caldecourt (December 1974). This patent describes an electrically resistive bridge element assembly comprising a thin metal strip folded into two arms and forming the bridge itself, one surface of one arm being immersed in the corrosive liquid and the other surface and arm forming the reference section. One advantage described for this design is that it provides temperature compensation.

A more comprehensive approach to monitoring corrosion is described in U.S. Pat. No. 3,936,737 Jefferies (February 1976), which describes a electrically resistive multi-element device that purports to eliminate the temperature dependence and provides for extended element life.

Electrical resistivity of metals usually is very low and therefore resistance changes in the sensor element that occur during corrosion are very small. This causes the sensitivity of such devices to be poor. Typically, detection of the slight amounts of metal lost per hour, which may be in the region of millionths of an inch per hour, gives rise to short term probe resistance changes of less than a micro-ohm. Data is extremely temperature dependent and the measurement of these small resistance changes yields signal-to-noise ratio problems, giving rise to practical limitations in detection limits.

Further improvements in electrical resistance corrosion probes are disclosed in U.S. Pat. No. 4,019,133 (April 1977); U.S. Pat. No. 4,217,544 (August 1980); and U.S. Pat. No. 4,326,164 (April 1982), all of which made progress in design, both mechanically and electrically, with the intention of elimination of the effects of temperature changes.

U.S. Pat. No. 4,338,563 (June 1982) discloses a secondary temperature compensation method that compensates for temperature differences between corrosion monitoring element and reference element, as well as fluid temperature compensation. It is known that measuring the resistance itself causes local probe heating; and the corrosion reaction itself can cause some chemically derived temperature fluctuations.

U.S. Pat. No. 4,587,479 (May 1986) discloses a multiple compensation method that further improves the usefulness of electrical resistance corrosion probes.

The creation and use of resistance probes have been prolific and such probes are available commercially and are in common use. They have been applied within many different industries and used for both aqueous and non-aqueous systems. One important issue with the resistance monitoring of metals to determine corrosion rate is how the resistivity of the metal changes with temperature. Fluids, such as ICE (Internal Combustion Engine) oils, may be at operating temperatures up to 120° C. or higher. The resistivity of some metals, for example lead, changes significantly within a typical ICE engines operating temperature range. A system monitoring the resistance of a lead electrode for example would detect a much greater change in resistance within the temperature range, than change due to low levels of corrosion.

ASTM G 31-72 (Reapproved 1995) is a Standard Practice for Laboratory Immersion Corrosion Testing of Metals and describes in detail how to avoid the pitfalls while performing laboratory tests, and is a very useful source of reference material for such tests.

Many standards have been initiated and adopted for monitoring corrosion rates. ASTM D 1275-96a is a Standard Test Method for Corrosive Sulfur in Electrical Insulating Oils, that describes the observation of color and surface changes occurring in a thin copper sheet, when immersed in the oil under test. This method is qualitative only and is only able to classify samples as either corrosive, or non-corrosive.

ASTM G 102-89 (Reapproved 1994) is a Standard Practice for Calculation of Corrosion Rates and Related Information from Electrochemical Measurements. It provides guidance in conversion of electrochemical measurements to rates of uniform corrosion. It details Corrosion Current Density and Polarization Resistance topics and is a very useful reference in this field, as is ASTM G 3-89 (Reapproved 1994) the Standard Practice for Conventions Applicable to Electrochemical Measurements in Corrosion Testing.

U.S. Pat. No. 4,130,464 (December 1978) teaches us an electrochemical method of evaluating the corrosion rates of metals; and such methods have been standardized and are described in the subsequent Corrosion Standard Section.

ASTM G 96-90 (Reapproved 1995) is a Standard Guide for On-Line Monitoring of Corrosion in Plant Equipment (Electrical and Electrochemical Methods.) It details both the Electrical Resistance and the Polarization Resistance method that involves interaction with the electrochemical corrosion mechanism of metals in electrolytes in order to measure the instantaneous corrosion rate.

ASTM G 59-97 Standard Test Method for Conducting Polarization Resistance Measurements also is a useful reference for providing guidance in the measurements of Polarization Resistance, which can be related to the rate of corrosion of metals at or near their corrosion potential.

Measurement of the Acidity/Alkalinity (pH) of Oils

The measurement of the pH of oil is a field of considerable interest within the automotive and trucking industries. One of the most important uses is to detect the onset of corrosion, due to depletion of oil additives. An internal combustion engine (ICE) lubricating oil is manufactured by adding quantities of chemical additives to a base stock oil. The quantity and type of these chemical additives are dependent upon the particular engine application; for example spark ignition engines use different oil from diesel engines. It is relevant to list the chemicals additives according to function: viscosity modifiers, anti-wear additives, dispersants, detergents, antirust additives, antifoaming agents, pour point depressants, antioxidants and bearing corrosion inhibitors. The compounds particularly of interest used in diesel engine lubricants impart a base reserve to the oil and prevent corrosive wear by neutralizing the sulfuric other acids caused by combustion and oxidation products. Typical base reserve compounds include metal sulphonates, various dispersants, and corrosion inhibitors, such as zinc dithiophosphates.

Heavy-duty diesel engine oil is required to operate reliably over a wide range of temperatures and for a considerable period of time. The oil becomes contaminated with both soluble and insoluble products of combustion wear and atmospheric particles. Diesel fuels contain additives and contaminants that are transferred to the lubricating oil during the combustion process. An example of such a contaminant is sulfur. Sulfur is acidic, as are other combustion byproducts, such as nitrogen oxide compounds. The oil manufacturer adds a basic compound which neutralizes sulfur and other acidic compounds. Therefore, a certain quantity of reserve basicity is built into the oil. During use, this oil reserve basicity diminishes, until eventually it becomes fully depleted. At such time, unless further chemicals are added, the oil is at the end of its useful life and the acid nature of the oil will corrode engine components and cause excessive wear. It is most important to be able to detect the onset of this acidic condition.

The performance of the oil is critical to the life of a heavy-duty diesel engine and for many years attempts have been made to standardize these and other lubricating oils. ASTM D 5967-97 is a Standard Test Method for Evaluation of Diesel Engine Oils in T8 Diesel Engines that addresses in comprehensive detail the tests standard within the industry for oil performance.

On-Road and Off-Road fleets send oil samples taken at regular intervals to Oil Testing Laboratories, because monitoring such data is critical to the long term continued performance of such vehicles. The results available from such laboratory tests include Total Acid Number (TAN) and Total Base Number (TBN), which are measurements related to the pH of the oil and are indicative of the onset of component corrosion. Total Base Number (TBN) is defined as the quantity of perchloric acid expressed in terms of the equivalent number of milligrams of potassium hydroxide that are required to neutralize a given sample according the specific method used.

Current standards for measurement of TAN and TBN are limited to laboratory based equipment. ASTM D 664-95 a Standard Test Method for Acid Number of Petroleum Products by Potentiometric Titration and ASTM D 4739-96 a Standard Test Method for Base Number Determination by Potentiometric Titration are examples of current standards.

Attempts have been made to measure the TBN or TAN in situ on the engine itself, thus alleviating the need for dispatch of samples to the laboratory. U.S. Pat. No. 5,023,133, (June 1991) titled Acid Sensor is an example of the prior art for the measurement of pH or its equivalent. This patent discloses an electrically conductive polymer device, which senses changes of acidity in a non-aqueous medium and is particularly suitable for the determining the alkaline reserve in a motor vehicle lubricating oil. The organic polymer sensor is described as being mounted inside of an oil filter, and is replaced when the filter is replaced. The life of this sensor is not compatible with the modern extended drain intervals demanded from modern heavy-duty diesel engine vehicle operators. This sensor, like most pH sensing devices, needs to be renewed or regenerated at frequent intervals, as system poisoning takes place quite frequently.

U.S. Pat. No. 4,741,204 (May 1998), titled Measurement of the Depletion of the Basic Additives in Lubricating oil, describes a corrosion-linked method that monitors the electrical resistance of a sensor made of copper, lead, mixtures and alloys thereof. The resistance of the sensor indicates the corrosion rate, which is correlated to the depletion of the additives. This device is limited in sensitivity, because of the very small resistance changes encountered.

U.S. Pat. No. 5,146,169, (September 1992), titled Reference Electrode and a Pair of Electrodes for Detecting the Acidity or Basicity of Oil, discloses a reference electrode formed of lead, zinc, tin, indium, cadmium, magnesium or any alloy thereof, which is used with a responding electrode made of a conductive solid. The electrodes generate a potential difference that varies with the acidity or basicity of the oil or sample under test. This use of metal/metal oxide electrode to measure pH for aqueous systems has been known for many years.

Oil Deterioration Detectors

A further class of detectors used for monitoring the deterioration of oils is based upon the measurement of the dielectric constant of the oil itself. Changes in the capacitance of the oil are detected using a pair of spaced sensor capacitor electrodes that use the oil to be measured as the dielectric medium. Various forms of this device have been developed, an example is disclosed in U.S. Pat. No. 4,646,070 (February 1997). Whereas this and other similar devices measure or indicate oil deterioration, they are not specific to monitoring one parameter, such as acidity or basicity since they respond to changes in many aspects of the oil, such as liquid and solid contaminants. This and subsequent enhancements, such as using magnetic fields, are designed to identify more specific aspects of the deterioration of the oil for example magnetic or carbon particle quantification. It is important to understand that the prior art capacitance measuring devices use the oil under test is used as a dielectric medium.

The problems encountered with pH devices, when installed in "On-Line" or "In-Line" situations are their lifetime. "On-Line" is defined as being located in the operating machine, but away from the main flow, such as at the end of a sampling tube; whereas, "In-Line" is defined as being located within the main flow.

It is known to those experienced in the art of measuring pH that electrodes used for this purpose become poisoned easily and, therefore, need to be regenerated quite frequently. Any device used in extended operation must be reliable and not give false indications. Poisoned electrodes do not give correct pH indications.

As the pH, or acidity/basicity of insulating oils is related to the corrosion of a metal electrode surface in this work, poisoning can be a relevant issue. U.S. Pat. No. 4,566,949, (January 1986), details a rapid method for cleaning an electrochemical detector and provides good background understanding of cleaning metal electrode surfaces by applying an electrical waveform that both oxidizes and reduces.

SUMMARY OF THE INVENTION

The present invention provides a method and apparatus for monitoring, for example, the corrosion rates of conducting materials, when immersed in electrically non-conducting or conducting fluids. The resulting data can be subjected to subsequent interpretation, using pre-determined correlation data, to yield the fluid acidity or alkalinity, presence of a specific chemical or contaminant. The invention is particularly suitable for use with insulating fluids, such as mineral and synthetic oils. Conducting materials are chosen to be modified, for example corroded or soluble by the test fluid, and form the electrode plates of a capacitive sensor, when these plates are coated or attached to a modern electronic dielectric medium. This dielectric medium is chosen such that it and the electrodes form a capacitor with an easily detectable capacitance value, for example 50 nF. At least one electrode of the capacitive sensor is located in the fluid stream, such that there results a plate dissolution modification, erosion, or corrosion modification to one or both of the plate electrodes. This plate modification is detected as a reduction, or apparent change in plate area, giving rise to an easily detectable capacitance change. The capacitance change detected is related to rate of erosion, dissolution or corrosion, i.e. modification and, therefore, the concentration of the contaminant and/or specific chemical of interest. It is not necessary to use two electrodes that are modified; nor is it necessary to electrically expose more than the one electrode for capacitive modification by the fluid under test.

The presence of a less insulating emulsified fluid within the electrically non-conducting fluid, for example glycol or water in oil, is detectable as an increase in the measured capacitance by all of the sensors described herein.

In the preferred embodiment of the invention, the electrode plate material is coated upon a piezoceramic material, such as Lead Zirconate Titanate (PZT), which has both a suitable dielectric constant and forms a piezo responsive element. The advantage of using PZT or other piezoceramic material in conjunction with a suitable electrode material is its ability to form an ultrasonic transducer element. Ultrasonic vibration is used to accelerate the dissolution, erosion or corrosion, i.e. capacitive modification of the electrode plates, thus giving a considerable ability to optimize the sensitivity. Summation of the ultrasonic energy provided to the PZT sensor plate is recorded and correlated to the rate of plate modification.

Further details and advantages of this method and sensor will become more apparent in the following description and the accompanying drawings.

BRIEF DESCRIPTION OF THE DRAWINGS

FIG. 1b is a perspective view of the sensor of FIG. 1a;

FIG. 1c is a side view of the sensor of FIG. 1a;

FIG. 2a is an exploded isometric drawing of another embodiment of the capacitive sensor device as described in this invention;

FIG. 2b is a perspective drawing of the capacitive sensor of FIG. 2a;

FIG. 2c shows a side view of the capacitive sensor of FIG. 2b;

DETAILED DESCRIPTION OF THE INVENTION

Figure 1A:
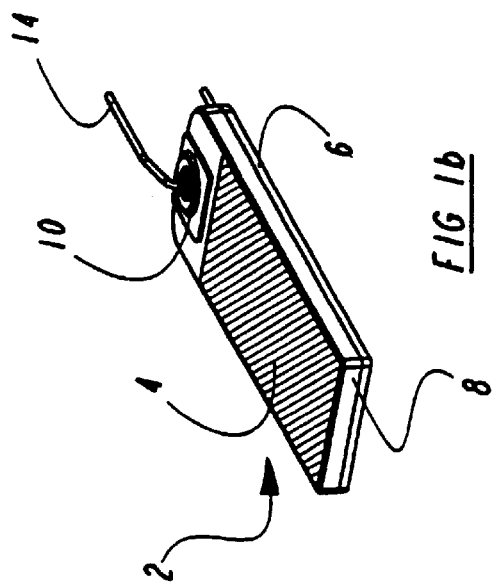
FIG. 1a is an exploded isometric view of the preferred capacitance sensor of this invention.
Figure 1B:
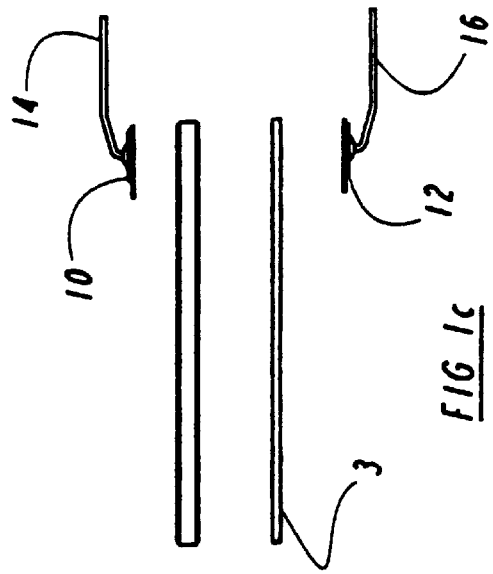
Figure 1D:
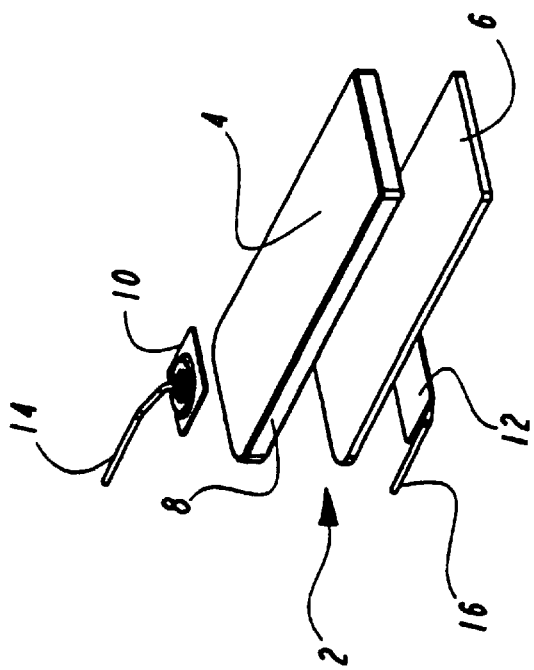
FIG. 1d is a side view of the sensor of FIG. 1b.
Figure 1C:
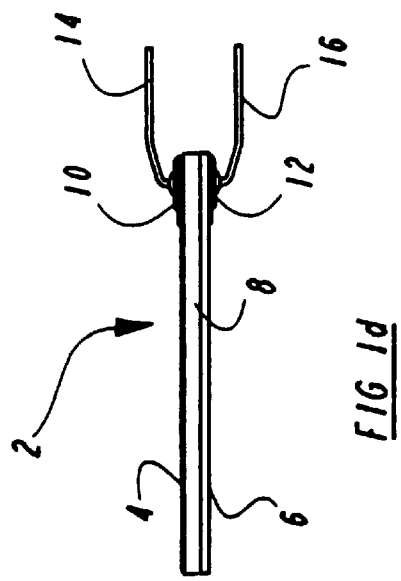

The present invention provides a method and device for measuring the modification, for example by dissolution, erosion or corrosion of electrically conducting materials in a non-conducting fluid under test for acidity, basicity or concentration of specific chemical species. Data may be obtained directly in an on-line or in-line situation, with conducting electrode materials and with non-conducting fluids. Data can also be obtained off-line with conducting fluids, but not on-line, in-line or in situ determinations. Measurements of the modifying activity of the electrode material(s) caused in conducting fluid must be taken following removal of the from that fluid.

Typically, data is obtained for metal or other electrically conducting solids in a flowing stream of fluid, such as lubricating or hydraulic oil. If required, the dissolution, erosion or corrosion, i.e. the electrode modified resulting data is interpreted to yield the fluids' acidic or alkaline strength in a form analogous to aqueous pH.

The conducting electrode or plate material is attached to either one or both of the sides of a formed solid dielectric sheet. If the conducting electrode material of interest is attached to one side of the dielectric sheet, then an additional electrically conducting plate must be attached to the sheet's second side. Both conducting plates become the electrodes that, in conjunction with the dielectric sheet, form a capacitor.

From conventional electrostatics, the capacitance in Farads of a capacitor C, can be determined from:

$$C = \frac{\varepsilon \cdot A}{d} \quad (1)$$

Where:

$\varepsilon$ is the permittivity of medium between the capacitor plates, $Fm^{-1}$;

A is the area of plates, $m^2$;

d is the separation of plates in meters.

The sensor according to the present invention is constructed in a similar way to a conventional capacitor. Referring to FIGS. 1a–d which show exploded and other views of a sensor 2 with electrodes 4 and 6 made from the metal or metals of interest. The electrode material must corrode, erode, or dissolve in the fluid being tested. As the electrode (s) is corroded by mechanisms such as dissolution or erosion, the electrode plate area decreases, as indicated in the example in Table 1.

TABLE 1

VARIATION OF CAPACITANCE WITH AREA OF ONE ELECTRODE

| Capacitance (nF) | Area (mm²) |
|---|---|
| 12.7 | 190 |
| 9.85 | 135 |
| 6.70 | 85.2 |
| 3.73 | 48.4 |
| 2.02 | 23.9 |

If the electrode 4, 6 corrodes with a uniform surface, action such as oxidation, the area of the plate need not decrease, although a capacitance change is detected. A uniform corrosion mechanism, such as oxidation, modifies the electrode surface and forms an oxide layer that acts as an additional dielectric. This additional metal oxide dielectric layer changes the overall capacitance of the sensor 2 according to the properties of the oxide and electrode area corroded. An increase in oxide layer thickness on an electrode surface generally results in a decrease in the sensor's capacitance. It is well known that two capacitor values, C1 and C2, in series results in a value lower than either of its two components according to the formula 1/C=1/C2+1/C2.

The medium used for the 'dielectric plate' 8, between the capacitor electrode plates 4, 6 should have a relative permittivity (@1 KHz) value within the range of 50 to 50,000, more preferably between 100 and 10,000 and most preferably within the range of 300 to 2000. Use of materials with relative permittivity values lower than approximately 50 leads to low sensor capacitance values and measurement of accurate values becomes a concern. To compensate for this, sensors with a larger area of electrode/dielectric plates have to be used. Sensors that have dielectric mediums with high relative permittivity values give high capacitance readings and large changes with temperature. Table 2 gives some typical relative permittivity (dielectric constant) values for ceramic materials. The capacitance of the sensor is determined by the size of the smallest electrode as indicated in Table 1. The relative permittivity is also important in deciding the capacitance of the sensor device, but care should be taken in choice of the material used.

TABLE 2

DIELECTRIC CONSTANT VALUES FOR SOME CERAMIC MATERIALS*

| Aluminum Oxide | 9.34–11.54 at 24° C. |
|---|---|
| Titanium Dioxide, Rutile | 86–170 at 27° C. |
| Lead Titanate | 200 at 24° C. |
| Lead Telluride | 450 at 24° C. |
| Potassium Niobate | 700 at 24° C. |
| Barium Titanate | 1200–1600 @ 1 kHz |
| Tin Telluride | 1770 at 24° C. |
| Lead Zirconate Titanate | 1800 @ 1 KHz |
| Lead Magnesium Niobate | 10,000 at 24° C. |
| Potassium Tantalate Niobate | 34,000 at 0° C. |

*From CRC Handbook of Chemistry and Physics 79th Edition 12-48 - 12-56

The dielectric medium must be non-reactive in the fluid of interest; it should be chemically inert and insoluble in the fluid(s) of interest. Its relative permittivity, its thickness and the overall size of the dielectric sheet/electrode plates should be chosen to construct a sensor with a capacitance value easily measured accurately with a capacitance meter or capacitance measuring circuit. Most dielectric materials in use today change their dielectric constant with temperature.

Figure 9:
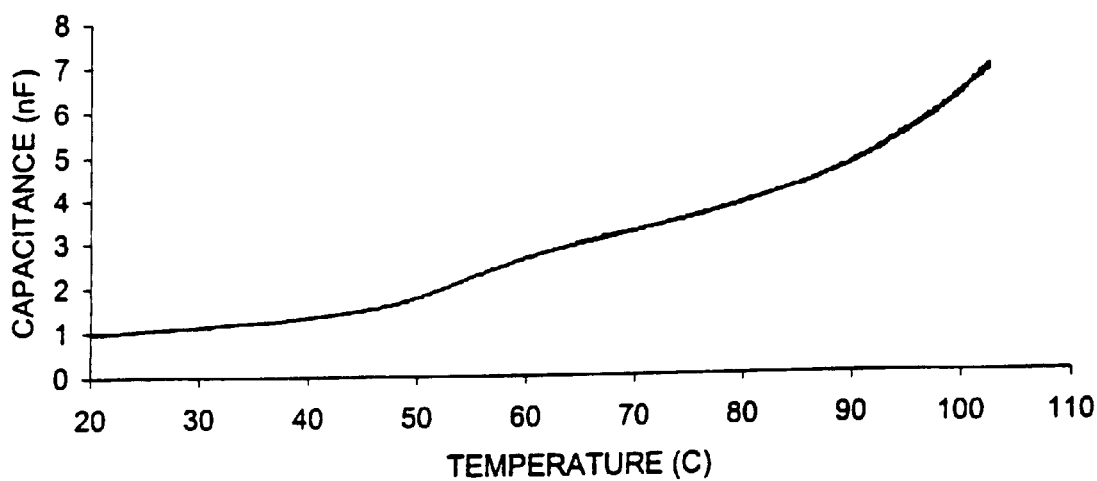
FIG. 9 is a graph with data for the change in capacitance reading with temperature for a niobium sensor immersed in engine oil.

Choosing a sensor dielectric material which changes a minimum amount with temperature is advantageous, so that changes due to corrosion are not masked by a high temperature change coefficient. FIG. 9 illustrates the capacitance change in engine oil for a niobium coated sensor within the temperature range of approximately 30 to 15° C.

Dielectric capacitor plates should be made by one of the several methods used within the electronics industry and those skilled in the art. These methods are detailed in many ceramics processing reference books, for example, Principles of Ceramic Processing $2^{nd}$ Ed. James S. Reed, Wiley-Interscience, New York.

The primary factor that determines electrode choice is its reactivity or activity in the fluid or fluid component of interest. Preferably, the conducting plates are metallic and are both made from materials that will corrode in fluids of interest. The plates should have a good electrical conductivity to enable them to function as capacitor electrodes. Most metals are suitable for use as plate materials. An Electrical Resistivity within the range of <1 to >15 ×10$^{-8}$ W-cm is suitable. A table of electrical resistivity values is available in the CRC Handbook of Chemistry and Physics, $79^{th}$ Edition, CRC Press page 12–45. Diesel engine lubricating oil becomes contaminated with sulfuric and nitric acids, among other acidic compounds both inorganic and organic in nature. Metals that corrode in these acids would be good choices for sensor electrode material. Careful consideration of the choice of material for electrodes 4, 6 can lead to specific chemical sensitivity. The two electrode plates may be made from different materials and each can be made sensitive to different materials; thereby, a sensor device specific to this chemical species or that chemical species is created. Ideally, to simplify the situation, each sensor device is made specific to a particular chemical species or pH detection level.

Another factor to consider is whether a good electrical contact 10, 12 can be made with the electrode. The formation of a passive metal oxide layer, which occurs rapidly in air with some metals, can complicate the attachment of the conducting cables 14, 16 needed to make the electrical connection to the sensor device 2.

In the consideration of the reactivity of the electrode material, possible corrosion mechanisms can be evaluated by reference to electrochemical or standard electrode potentials. It is important to consider any electrochemical behavior that the electrodes 4, 6 might have with each other and with other metals used or found within the system under test. The Standard Electrode potential of the metals of interest can be useful to help assess any of these possible interactions. Table 3 lists a few Standard Electrode Potentials at 25° C. These electrode potentials are quoted for aqueous systems and therefore should only be used as a guideline to assist in the assessment of probable interaction. Almost all of the tabular data available is for aqueous systems and non-aqueous reference data is not readily available.

TABLE 3

STANDARD ELECTRODE POTENTIALS FOR AQUEOUS SOLUTIONS AT 25° C.**

| Aluminum | $Al^{3-} + 3e^- = Al$ | −1.66 v |
| Zinc | $Zn^{2+} + 2e^- = Zn$ | −0.763 v |
| Iron | $Fe^{2+} + 2e^- = Fe$ | −0.440 v |
| Nickel | $Ni^{2+} + 2e^- = Ni$ | −0.250 v |
| Tin | $Sn^{2+} + 2e^- = Sn$ | −0.136 v |
| Lead | $Pb^{2+} + 2e^- = Pb$ | −0.126 v |
| Copper | $Cu^{2+} + e^- = Cu^+$ | +0.17 v |

TABLE 3-continued

STANDARD ELECTRODE POTENTIALS FOR AQUEOUS SOLUTIONS AT 25° C.**

| Copper | $Cu^{2+} + 2e^- = Cu$ | +0.34 v |
| Copper | $Cu^+ + e^- = Cu$ | +0.52 v |
| Silver | $Ag^- + e^- = Ag$ | +0.7991 v |

**Physical Chemistry $3^{rd}$ Ed., Castellan, G. W. Addison-Wesley Publishing Company, Reading, Ma, p381.

Niobium, a refractory metal, is considered a chemically stable element. It is inert in acids, its oxide is mildly acidic, and it is sensitive to most alkalis, particularly at elevated temperature (98° C.). Therefore niobium is suitable for detecting alkali concentrations. Niobium has an electronegativity value of −1.6 and electrical resistivity of 15.2×10$^{-8}$ W-cm at 273 K. When used for an electrode material, the formation of a surface oxide layer increases the overall electrical resistivity of the niobium sensor. The oxide layer acts as an additional dielectric substrate and forms an additional capacitor in series with the sensor and its surroundings. This reduces the indicated capacitance value and the rate of change in its value is a measure of the rate of oxide formation, which can be correlated to alkali strength.

Indium is stable in alkali solutions, but is sensitive to acids. Indium has an electronegativity value of 1.78 and electrical resistivity of 8.0×10-8 W-cm at 273 K). It is suitable as an electrode 4, 6 for detecting acid concentrations.

Aluminum is reactive to alkalis and dissolves in strong aqueous solution. This inventor has found that a similar action takes place in lubricating oils that contain basic compounds. The action is slight, but a sensor that uses an aluminum leaf sensor approximately 1–2 mm thick completely dissolved at 120° C.

Copper on first examination would be a good choice and indeed has been used for resistive corrosion elements, as discussed in the Background section. The problem with copper, however is that it dissolves in nitric and sulfuric acids, but only when exposed to the air. In addition, copper is attacked by alkalis, perhaps making it an overall poor choice, because of its non-specificity.

Lead is soluble in nitric acid and reacts in many other acids; however its own corrosion products form a protective film or coating, usually to protect it. Lead has a standard electrode potential, EPb2+/Pb=−0.126V, which shows that it is thermodynamically unstable in acid solution. Lead when tried as a sensor electrode material changed its resistivity so significantly, over the temperature range that special circuitry was needed to compensate for the enormous change in indicated capacitance.

The chemical reactivity will determine the thickness of the electrode plates 4, 6 needed for a certain sensor lifetime, i.e., the longer the sensor lifetime required, the thicker the plate. The area of the electrode plates (and the dielectric plate 8 and its thickness) determine the sensor capacitance according to Equation (1.) Typical sensor capacitance values can be within the range of 0.1 to 1000 nF. Higher or lower values may be used according to design circumstances. For example, a sensor had a capacitance of 21 nF, an electrode plate area of 250 mm$^2$ and a dielectric plate thickness of 0.05 mm having a relative permittivity of approximately 480.

Examples of metals that form passive layers are aluminum and niobium and good electrical connection to electrodes made from these metals is difficult, but achievable after cleaning and/or surface treatment.

The sensor electrodes can be made from different materials for example, electrode 4 may be made from copper and electrode 2 from aluminum. When using different materials for the electrodes care must be taken not to set up a non-intentional electrochemical system that gives false corrosion results related to the species of interest. Similarly, it is known by those experienced in corrosion problems that the presence of some chemicals, for example copper ions when in solution, markedly affects the corrosion rate of other materials.

FIGS. 2a–c show views of the sensor assembly 2' having wedge shaped electrodes 4', 6' suitable for extended operation of the sensor. Tapering the electrodes 4', 6' into this shape ensures that, as material is removed from the entire surface of the sensor electrode, the corrosion mechanism decreases the area of the electrode from the thin edge. Material removed from the entire surface of the wedge will reduce the electrode plate area at the thinnest end only. The dimensions of the wedge should be determined from the expected material loss during use and can be determined from empirical or reference data. Material thickness at the thin edge 18 of the wedge may be of the order of 1–2 micrometers or less, thickening up to a millimeter or more at the thickest edge 20. Evaluation of the corrosion rate of the electrode in the test fluid should be performed to construct a set of calibration data. This data is used to determine the exact dimensions of the sensor components. The sizes of the sensor components also are chosen according to other various factors. Apart from the required life of the sensor, another important factor is the volume of fluid used in the system. The test fluid volume will determine whether the chemical interaction itself changes the rate of interaction due to depletion of the chemical species under test. This is unlikely to be a problem, unless the fluid volume is small and the sensor size large. In addition, the test fluid volume influences how much contamination from electrode corrosion products is added to the system. It may be important not to contaminate the fluid with excess amounts of the sensor materials; under these circumstances, a small size sensor may be required. The quantity of sensor material that will end up within the fluid itself is simple to calculate, assuming the maximum electrode loss during the life of the sensor.

The larger the area of the sensor components, the higher the capacitance of the sensor created. It is desirable for the capacitance of the probe to be of sufficiently high value to be measured accurately by the electronic capacitance measuring circuitry and the capacitance changes that occur during operation of the sensor device.

Figure 3C:
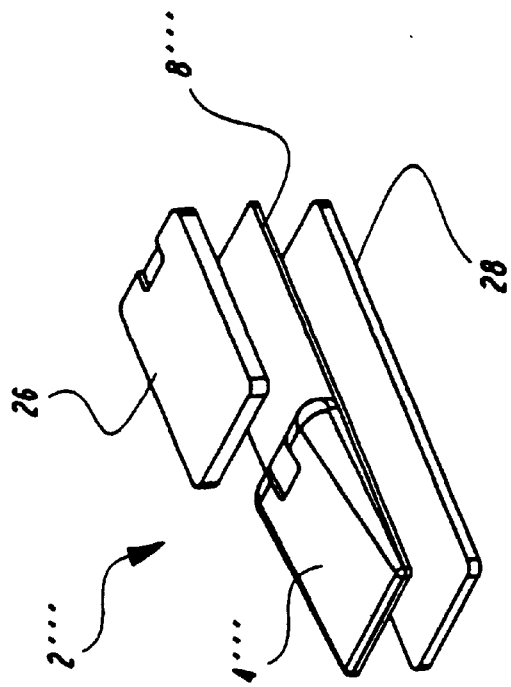
FIGS. 3a–d show two alternative embodiments of the sensor/piezoelectric transducer combination, using a common ceramic dielectric plate.
Figure 3D:
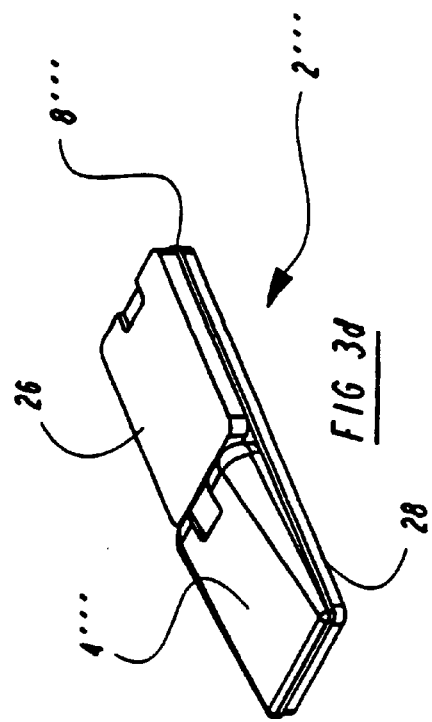
Figure 3A:
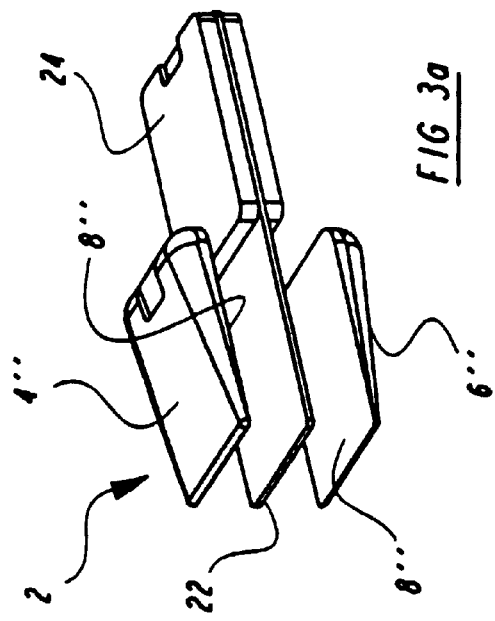
Figure 3B:
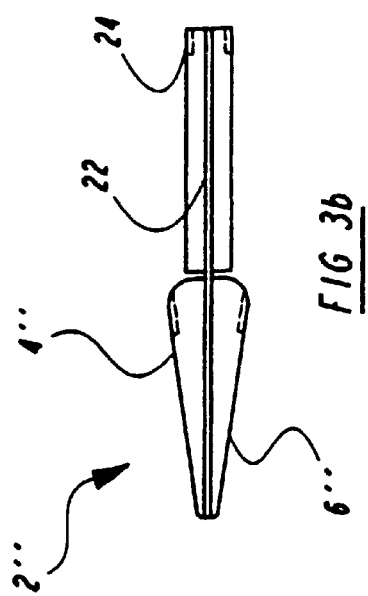

FIGS. 3a–d show further embodiments of the sensor, identified as 2" in FIGS. 3a and 3b and 2'" in FIGS. 3c and 3d. Sensor 2" employs a pair of wedge shaped electrodes 4" and 6" mounted upon dielectrics 8". Separating the two dielectrics is conductive member, such as brass 22, which is inserted into a piezoceramic element 24, which is set into vibration by electric circuitry (not shown in FIG. 3), and in turn sets the member 22 into vibration to accelerate the modification of the electrodes.

FIGS. 3c and 3d illustrate a hybrid sensor 2'", in which there is provided a conducting electrode 4'" on a dielectric 8'" and an electrode 26 that is non-reactive to the test fluid. A support plate 28 also is non-reactive in the test fluid and provides strength and rigidity to the sensor. The support plate 28, if conductive, can provide an electrical connection point for electrode 26.

Figure 4:
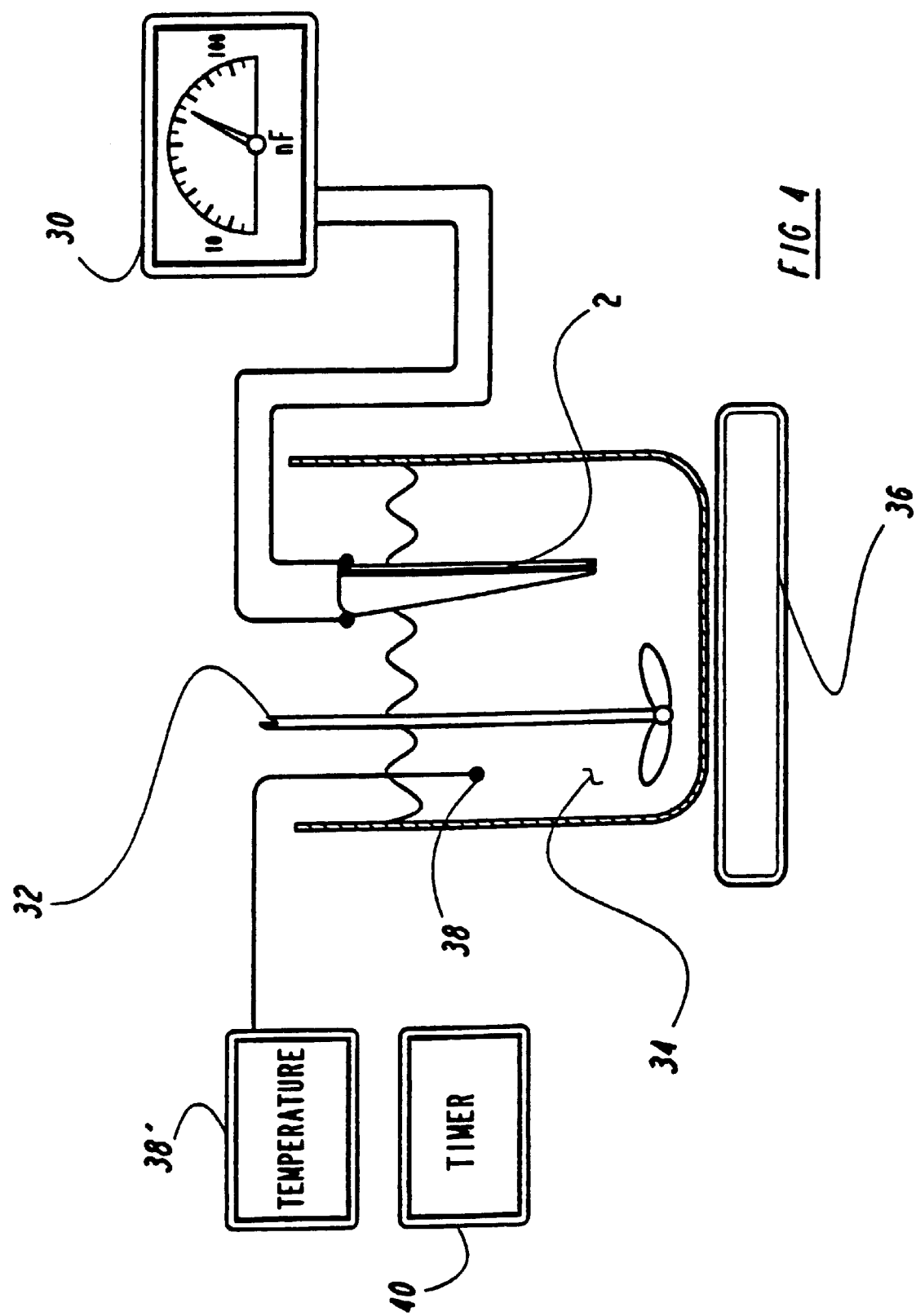
FIG. 4 shows a schematic for a laboratory-based corrosion measuring sensor assembly.

FIG. 4 illustrates the minimum laboratory equipment to perform the method of the invention, having a sensor 2, which is connected to a capacitance meter 30 with a measurement range suited to the capacitance value of the sensor; this range typically 0 to 100 nF. Stirrer 32 is used to ensure even mixing and heat distribution within the fluid 34 under test. The test fluid is heated with heater 36 and the temperature is recorded using a temperature probe/meter combination 38.

The method of the invention should be performed by recording the capacitance of the sensor 2 at the temperature of operation and with a zeroed exposure timer 40. The test fluid should be stabilized at the test temperature before the sensor is immersed. It is not necessary for the sensor to have been unused, since the method involves the measurement of the rate of change of recorded capacitance values.

TABLE 2

VARIATION OF SENSOR CAPACITANCE WITH TEMPERATURE

| Temperature (° C.) | Capacitance (nF) |
|---|---|
| 37.8 | 21.9 |
| 40.6 | 22.4 |
| 44.4 | 22.7 |
| 48.9 | 23.2 |
| 51.7 | 23.6 |
| 57.2 | 24.2 |
| 61.7 | 24.8 |
| 65.6 | 25.2 |
| 71.1 | 26.0 |
| 76.7 | 26.8 |
| 82.2 | 27.6 |
| 87.8 | 28.4 |
| 93.3 | 29.2 |

It is important that the temperature of the test fluid be known, since the indicated capacitance can vary considerably with the temperature of the sensor. Table 2 shows the variation of capacitance with temperature for a sensor 2 with copper electrodes 4, 6. Most of this variation is caused by changes in the relative permittivity (dielectric constant) of the dielectric plate 8. Therefore, the temperature/capacitance data may be used to determine the "blank" for the sensor and, as long as the temperature is recorded a correction based upon the correlation determination can be made.

Having chosen a suitable sensor electrode material for the detection of acidity/alkalinity, a contaminant or a specific chemical, a correlation must be determined which gives the rate of change of capacitance at different concentrations (of the acidity/alkalinity, contaminant or chemical grouped hereinafter by the term species).

Figure 8:
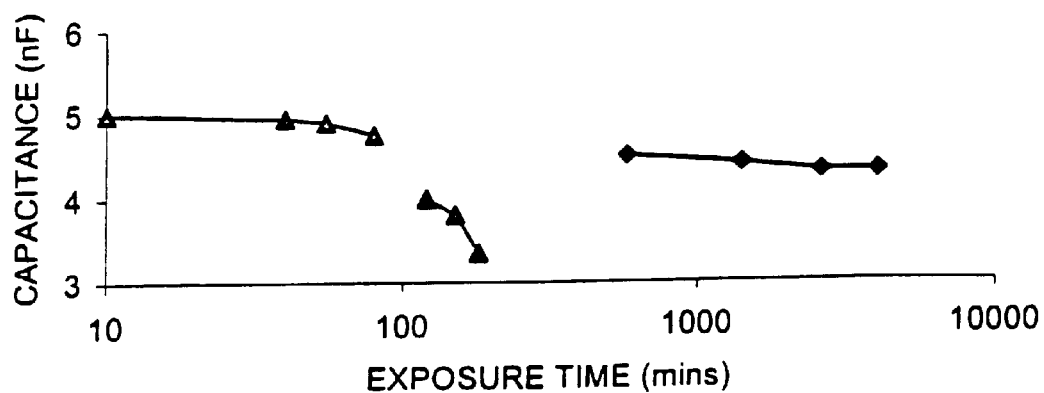
FIG. 8 is a graph of capacitance change vs. time when using an aluminum foil sensor immersed in engine oil at 120° C. Plot A without ultrasonic vibration shows a gradual decrease with time; whereas, plot B shows a increase in rate of decrease, when the sensor is subjected to ultrasonic vibration.

Such a calibration is illustrated for unused heavy-duty engine oil in FIG. 8. line A. It is a graph of capacitance against oil immersion/exposure time at the conditions of the test, for a single concentration of the interested species within the oil. This data represents the response of the sensor to alkali species in the test oil. This calibration should be performed at different calibrated concentrations of the interested species.

Measurement of the capacitance and detection of the changes that occur during use of the sensors 2 can be accomplished with commercially available capacitance meters 30. The electronic circuitry used commonly in these devices applies voltage pulses to the capacitor in a test that determines the resistance/capacitance (RC) time constant. The RC constant may be considered as the charging rate of the circuit. The application of the RC voltage pulses that are used for monitoring the corrosion of the sensor can increase its rate of corrosion by exceeding the corrosion potential at is the sensor's surface. This may be beneficial, or not, according to requirements. The applied voltage pulses also can be used to vibrate a sensor 2" that is piezoelectrically active.

In FIG. 8 line B shows a calibration line for the same sensor configuration 2" as shown in FIG. 3a, in which cumulative ultrasonic vibration time is plotted against capacitance. The rate of change of capacitance is much greater with the use of ultrasonic vibration. The purpose of applying ultrasonic vibration energy to the sensor is to provide the ability to more rapidly "react" the sensor in the fluid of interest, which gives some control over the reaction rate of the sensor in the fluid 34. The calibration shown in FIG. 8 line B was performed with constant ultrasonic power application; most ideally, the calibration should involve the electrical power applied. The applied ultrasonic vibration provides the addition of mechanical energy that increases the rate of corrosion reaction. While the application of ultrasonic energy provides a more rapid rate of erosion, care must be taken to ensure that a "blank" determination is known since, some fragile electrode materials can be eroded simply from this additional energy input.

It is important not to confuse capacitance changes caused through changing the sensor temperature with changes caused by corrosion. FIG. 9 is a graph of niobium sensor capacitance readings, while immersed in engine oil, throughout the temperature range of 20 to 105°.

Figure 10:
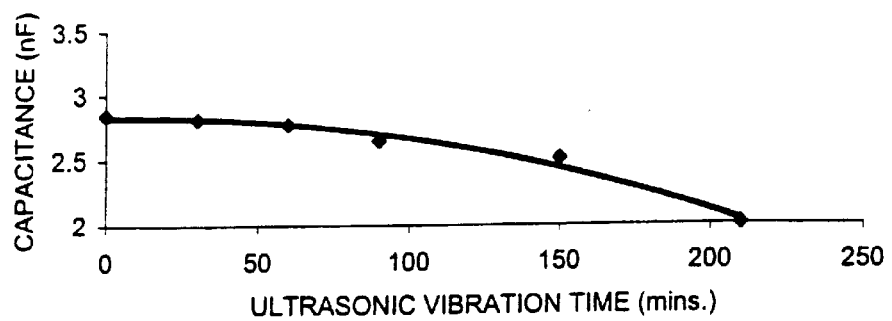
FIG. 10 is a graph showing an example calibration plot of niobium sensor capacitance vs. ultrasonic vibration time.

FIG. 10 shows an example of a calibration line for niobium in engine oil, using ultrasonic vibration. Here, niobium is being responsive to alkali species present in the oil that is maintained at a constant temperature.

In addition, the use of ultrasonic vibration can be used to "de-passivate" the electrode surface. Some metal oxides are known to form passive layers under certain chemical conditions, for example aluminum forms a passive oxide layer in the atmosphere and at aqueous pH values of less than approximately 8. With the sensor illustrated in FIG. 3, ultrasonic vibration can be used to "clean" the metal surface, thus exposing further surface for corrosion. Furthermore, the rate of change in the measured capacitance that occurs with a sensor made from a metal/passive metal oxide combination can be correlated with the alkalinity/acidity or chemical of interest. What is required for passivity is a rapid rate of formation of the oxide layer and a slow dissolution rate. The passive surface may be cleaned by the application of ultrasonic energy. Following this surface cleanup, the surface will passivate again and the rate at which this occurs is proportional to the concentration of the species of interest. Not all passivation films will be removed by such action. It is believed that the use of the additional mechanical energy in the form of ultrasonic vibration allows dissolution of the passive film layer that may be just a few nanometers thick. Rapid dissolution of the passive layer makes room for further formation of an oxide layer, thereby increasing the rate of reaction.

Figure 11:
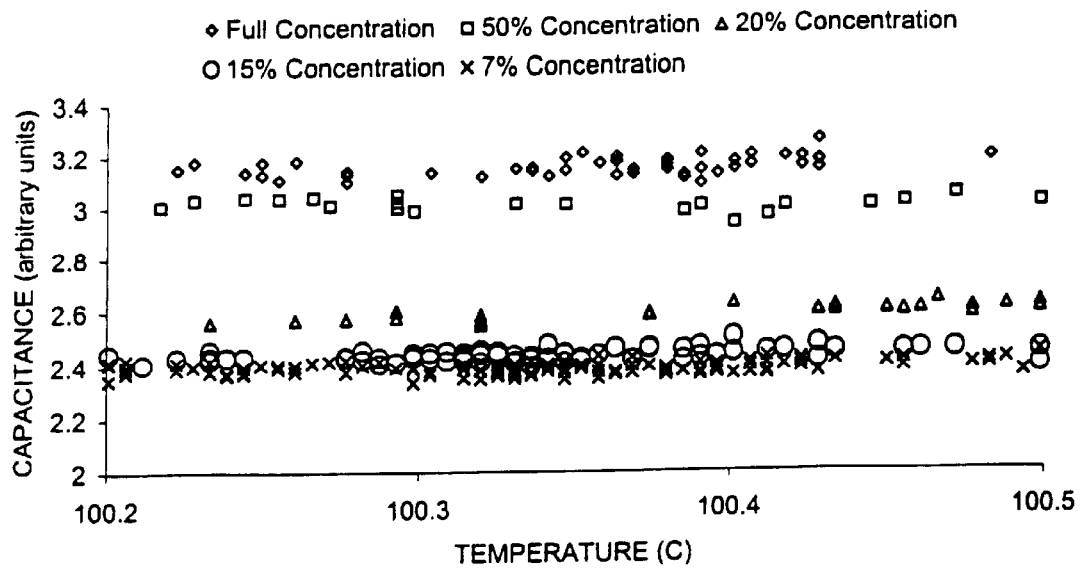
FIG. 11 shows data recorded at shows capacitance data recorded for engine oil with different alkali content (TBN) vs. temperature.
Figure 12:
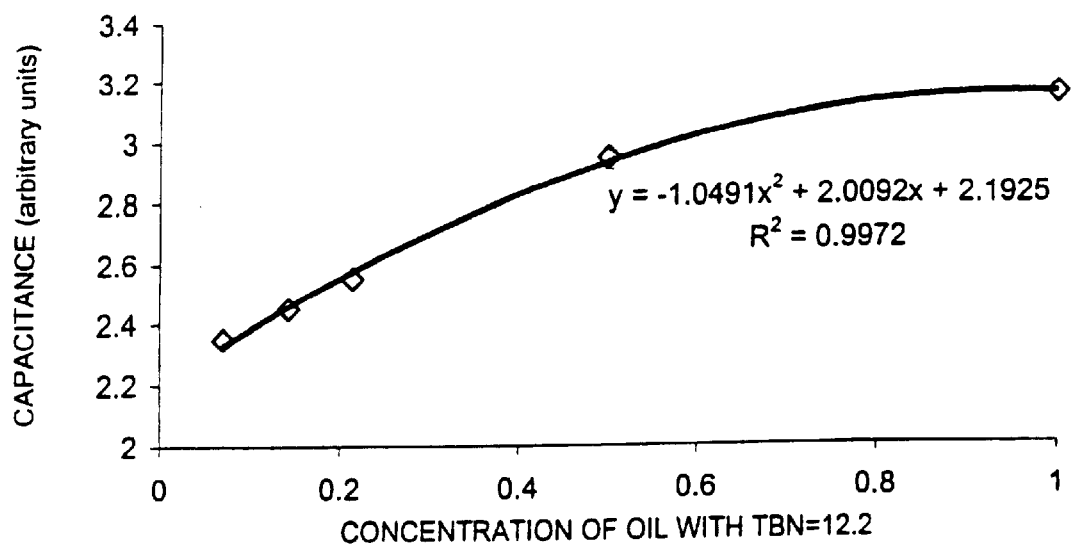
FIG. 12 is a calibration graph showing niobium sensor data obtained from the FIG. 11 data set, at one temperature and correlated against dilution of a oil with a TBN of 12.2; and, FIG. 13 is a graph showing the increase in capacitance of an indium sensor in engine oil caused by the presence of a 0.1% glycol/water emulsion.

FIG. 11 is a graph of niobium sensor data obtained for different alkali concentrations within engine oil. These sample oils were created by diluting a heavy-duty engine oil that contains "an additive package" giving a TBN of 12.2, with different volumes of straight mineral oil. The data for each alkali concentration was obtained without applying ultrasonic vibration, over a relatively short time period of a few minutes. The capacitance was measured continuously and the data shows a decreasing capacitance with increase in dilution of the oils additive package.

Modern engine oils, which contain many additives that coat and protect metal surfaces against corrosion, can give different calibration data for the sensor. Interpreting this data is necessary for each different test fluid/system. In practice, differences between "blank" readings for oils from different manufacturers is small and these differences are not significant, since changes in capacitance with time is more is important than instantaneous values. The application of ultrasonic vibrational energy with a sensor such as 2" provides control of the reaction rate.

During use the sensor capacitance should be monitored and its rate of change can be used to determine the concentration of the species of interest from the calibration data. If during use, the rate of change of capacitance is too low to provide data, ultrasonic power is applied and the 'second' calibration data then must be used.

Figure 13:
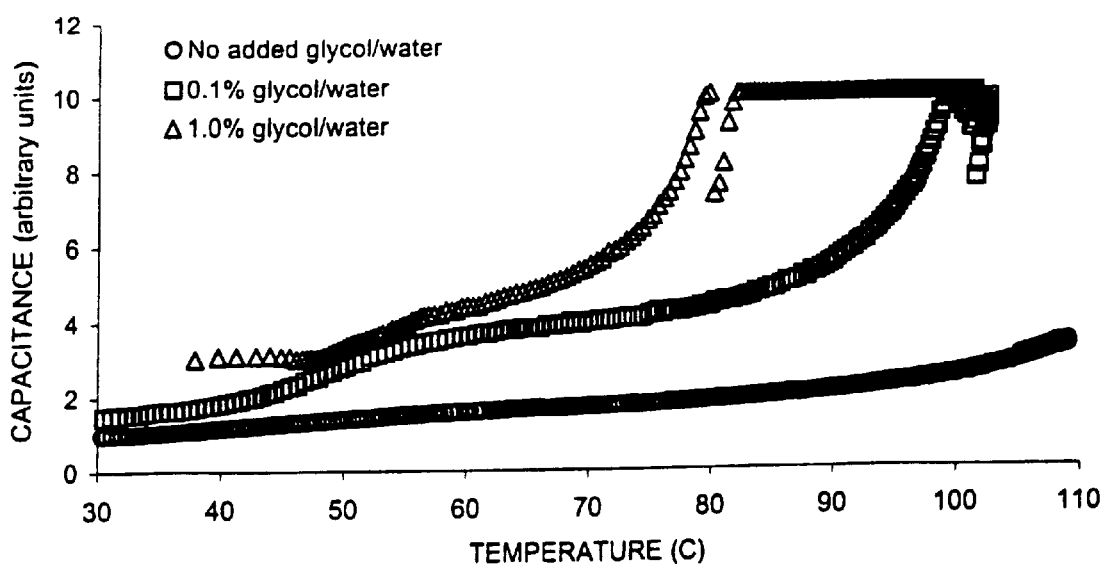

The sensors 2', 2", 2'" and similar capacitive sensors, with or without corroding electrode(s), when used in non-conductive oil for example, can detect the presence of more conductive materials within the test fluid. Emulsified liquids, such as glycol and/or water present in the test fluid are easy to detect with these sensors. If an ICE gasket fails, a release of water and/or glycol can suddenly be released into the lubricating oil; if this condition is not detected rapidly, a catastrophic engine failure can occur. These sensors are able to detect the emulsion caused by such a release of glycol and/or water, for example. FIG. 13 is a graph showing data for an indium coated sensor 2 immersed in engine oil and heated throughout the temperature range of 30 to 110° C. Three separate "runs" provide data for no-added glycol/water, 0.1% by volume added glycol/water, and 1.0% by volume added glycol/water. As the temperature is increased, the imiscible glycol/water forms emulsion particles with decreasing size. The deviation for the "emulsion data sets" becomes larger as the number of emulsion particles increases. If the emulsion partially dissolves in the test fluid, the capacitance readings will decrease somewhat, as is indicated at the higher temperatures for both of the glycol/water plots shown in FIG. 13.

If the sensor 2, electrode 4 material, and its dimensions are chosen to create a highly reactive sensor responsive to the test fluid, and the sensor electrode 4 is covered with a protective coating, the presence of specific chemicals that dissolve this protective coating can be detected. Detection of the chemical occurs with the capacitance change that is detected after both the protective coating is dissolved and the sensor electrode 4 is modified by the test fluid. For example, electrode 4 material made from a thin coating of aluminum, that is protected by a polyethylene coating, can be used to detect the presence of toluene, xylene or other solvents in oil.

Figure 5:
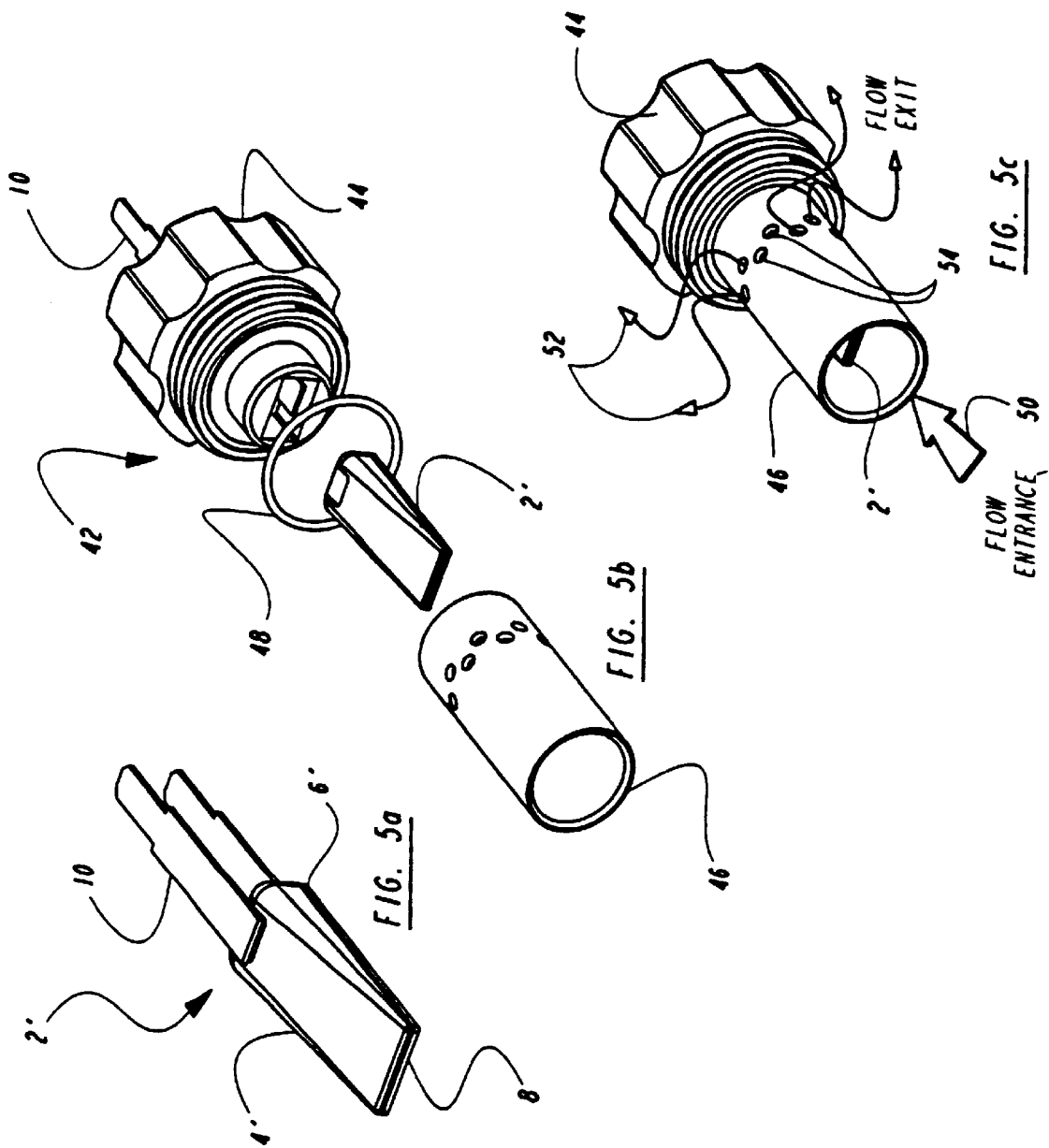
FIGS. 5a–c show isometric views of the assembled sensor/sensor-housing assembly suitable for use in an on board engine oil analysis system.

A preferred embodiment of this invention next is described with use of FIG. 5a–c to monitor the depletion of the alkaline base reserve of an ICE lubricating oil. When the base reserve is depleted, the oil becomes more and more acidic with continued use. Both alkaline and acidic conditions may be monitored with the method and device of this invention. FIG. 5b shows an exploded view of sensor 2' forming part of an assembly 42 suitable for installation in an on-line or in-line application with a threaded mounting 44, a protective sleeve 46, for the sensor 2' and an O-ring seal 48. FIG. 5c illustrates the flow path of the test through the assembly 42 by use of a flow arrow 50 into and over the sensor 2' and then exit arrows 52 from the peripheral holes 54 in the protective sleeve.

Figure 6:
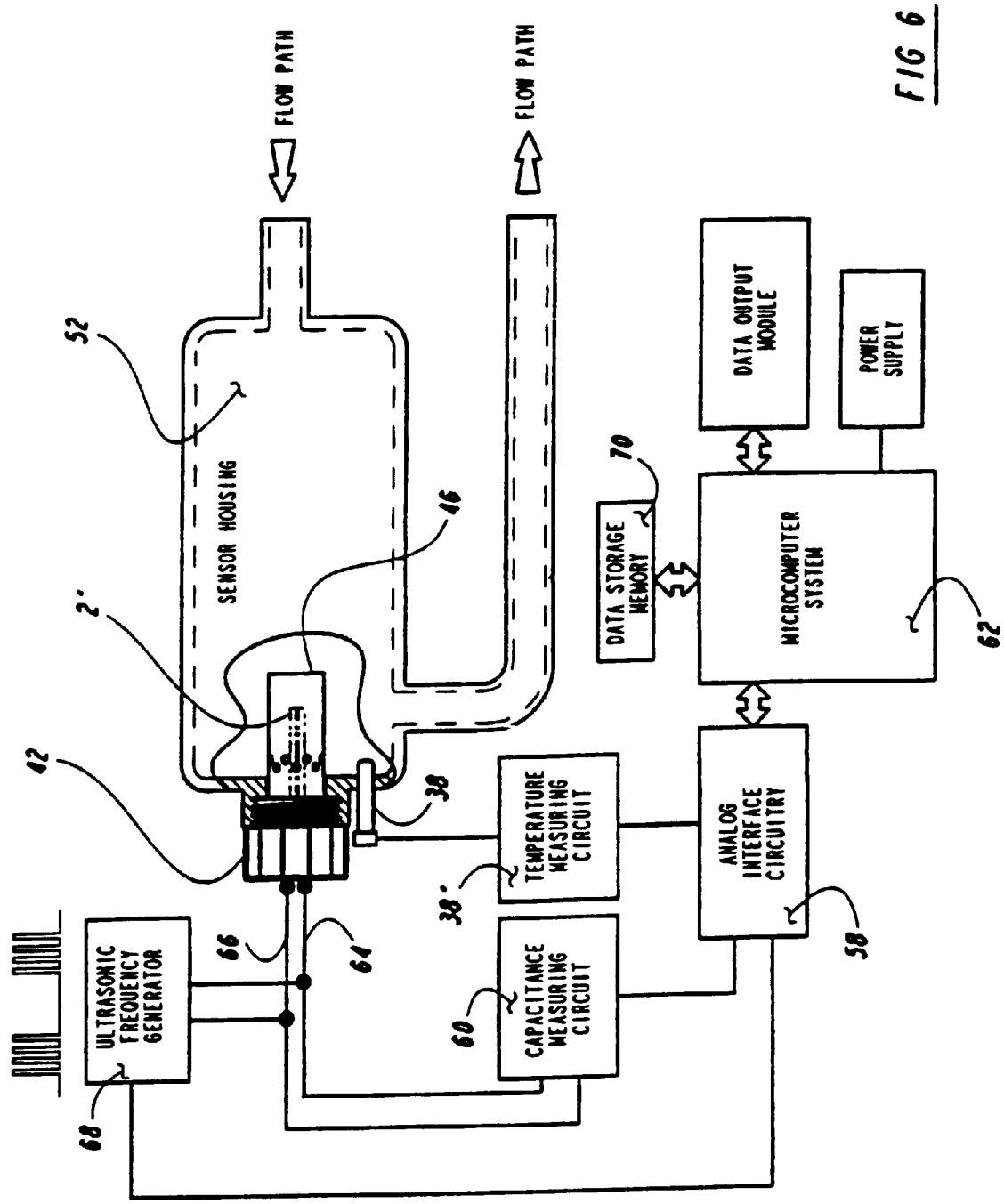
FIG. 6 shows a block diagram of the sensor/sensor housing configured in an on-board engine oil-monitoring device.

The sensor assembly 42 is mounted in a housing 56 that is used to contain the test fluid flow as shown in FIG. 6. The illustrated flow path is representative of the passage of the non-conducting fluid, such as the ICE lubricating oil. The housing 56 is made preferably of relatively non-reactive metal, such as stainless steel. The sensor assembly is mounted in the fluid path and sealed with an O-ring 48 or other sealing mechanism (not shown in FIG. 6). A temperature measuring circuit 38' with probe 38 provides the system temperature to an analog interface circuit 58. The temperature probe 38 can be a thermocouple or platinum resistance thermometer device. The sensor 2' is connected to a capacitance measuring circuit 60 coupled to the analog interface circuit 58 of a microcomputer system 62. The sensor has two further connections 64, 66 from an ultrasonic frequency generator 68. The microcomputer 62 is used to form an intelligent system, in which the microprocessor reacts to the sensor capacitance output and if needed, provides ultrasonic frequency pulses at constant power for known periods. The system calibrations, as explained above, are stored in the data storage module 70, preferably in non-volatile memory, so that the data can be stored and recovered at any time. The sensor capacitance data is fed back to the system and continuous assessment of both the reaction rate and ultrasonic action needed is made. The means to implement this type of microcomputer/intelligent system is known to those skilled in the art of electronics/software implementation and is therefore not detailed herein.

Figure 7:
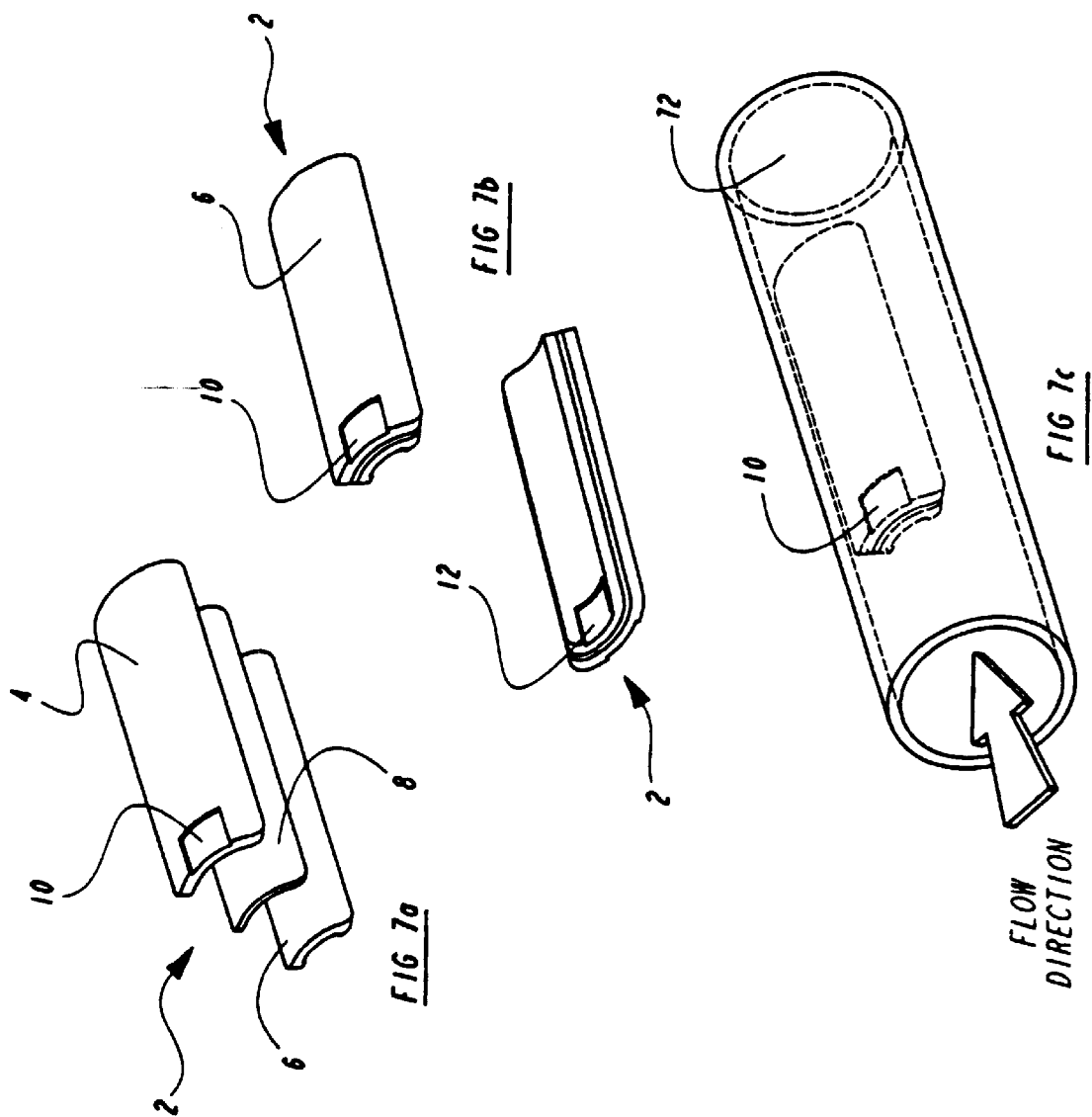
FIGS. 7a–c show an alternative embodiment of the sensor mounting, for use in a flowing stream within a pipe or tube.

A further embodiment of the sensor of this invention, shown FIGS. 7a–c, is suitable for use in a fluid containing tube. The sensor electrodes 4 and 6 and the dielectric plate 8 are curved. The sensor electrode connecting areas are 10 and 12 and FIG. 7c shows tubing 72 that might be used in a chemical or other processing plant.

While the present invention has been described in conjunction with specific embodiments thereof, it is evident that many alternatives, modifications, and variations of both the method and devices described will be apparent to those skilled in the art. Accordingly, it is intended to embrace all alternatives, modifications and variations that fall within the spirit and broad scope of the appended claims.

What is claimed is:

1. A sensor for electrically measuring at least the chemical characteristics of a test fluid, said sensor having at least one electrode in the test fluid comprising:
    at least two electrodes and a dielectric element:
        said dielectric element being composed of material different from the test fluid;
        said electrodes and dielectric element being mechanically and electrically assembled to form and operate as an electrical capacitor having measurable capacitance; and
        at least one of said electrodes being modified by the test fluid over a time period, so as to result in a measurable change in said capacitance of said sensor over that time period.

2. A sensor according to claim 1, in which:
said dielectric element is inert in the test fluid.

3. A sensor according to claim 1, in which:
said one electrode is of electrically conducting material.

4. A sensor according to claim 1, in which:
the modification of said electrode is by at least one of corrosion, erosion, dissolution and change of its resistivity.

5. A sensor according to claim 1 in which:
a second of said two electrodes is of a material different than said material of said one electrode.

6. A sensor according to claim 1, in which:
at least one of said electrodes has a wedge shaped profile, being thicker at a first end.

7. A sensor according to claim 1, in which:
at least one of said electrodes and said dielectric element are of a generally rectangular shape and are curved.

8. A sensor according to claim 1, in which:
at least one of said electrodes is non-reactive to the test fluid.

9. A sensor according to claim 1, in which said sensor further comprises:
a piezoceramic element, which can be set into vibration by electric circuitry, said piezoceramic element being mechanically coupled to at least one of said electrodes to vibrate it and thereby accelerate its modification.

10. A sensor according to claim 1, in which:
said dielectric element has a relative permittivity, at one kilohertz, within the range of 50 to 50,000.

11. A sensor according to claim 1, in which:
at least one of said electrodes, is of a material chosen to be employed in said sensor for use in a test fluid which is one of an insulating fluid and an electrically conductive fluid.

12. A sensor according to claim 1, in which:
said sensor is constructed and arranged to exhibit capacitive changes, when electrically conductive contaminants are present in the test fluid.

13. A sensor according to claim 1, in which:
said sensor is constructed and arranged to exhibit capacitive changes, when emulsified liquid is present in the test fluid.

14. A sensor according to claim 1, in which:
said sensor is coupled electrically to a microcomputer system and a capacitance measuring circuit,
whereby the changes in capacitance of said sensor over time are recorded for subsequent processing.

15. A method for electrically monitoring the characteristics of a test fluid, said method comprising the steps of:
    employing measuring, based upon changes over time, of at least one test fluid immersed electrode of a capacitor, said capacitor also having a dielectric element which is different from the test fluid;
    modifying, by at least said one of chemically, physically, and electrically at least said one electrode;
    said modifying being caused by changes over time of at least one characteristic of the test fluid;
    causing by said modifying measurable capacitive changes of said capacitor; and
    reporting said measurable capacitive changes.

16. The method according to claim 15, in which:
said modifying is in the form of at least one of corroding, eroding, dissolving and changing the resistivity of at least said one electrode.

17. The method according to claim 15, including the step of:
causing the test fluid, near the electrode to be of uniform distribution and known temperature during said monitoring.

18. The method according to claim 15, and:
subdividing said monitoring and said reporting into a plurality of known time periods extending over a significant span of time, so as to be able to be measuring slowly changing, as well as rapidly changing, characteristics of the test fluid.

19. The method according to claim 15, in which:

said measuring is of the rate of change of capacitance.

20. The method according to claim 15, further comprising the step of:

vibrating at least said one electrode, while immersed in the test fluid, thereby increasing the rate of capacitive change.

21. The method according to claim 15, further comprising the step of:

configuring the shape of said electrode to have a longer use.

22. The method according to claim 15, comprising the further step of:

establishing a relative motion of high velocity between said at least one electrode and the test fluid.

* * * * *